United States Patent [19]

Fine et al.

[11] Patent Number: 5,215,079
[45] Date of Patent: Jun. 1, 1993

[54] SINGLE DOSE METERED DOSE INHALER FOR DELIVERY OF VACCINES AND OTHER DRUGS

[75] Inventors: Jonathan M. Fine, Easton, Conn.; Michael E. Whitham, Great Falls, Va.

[73] Assignee: Armstrong Pharmaceuticals, Inc., New Canaan, Conn.

[21] Appl. No.: 884,800

[22] Filed: May 19, 1992

[51] Int. Cl.⁵ .............................................. A61M 11/00
[52] U.S. Cl. .......................... 128/200.14; 128/200.23
[58] Field of Search .................... 128/200.14, 200.23; 222/160, 162, 402.2, 402.14

[56] References Cited

U.S. PATENT DOCUMENTS

| | | | |
|---|---|---|---|
| 4,834,083 | 5/1989 | Byron et al. | 128/200.23 |
| 5,027,808 | 7/1991 | Rich et al. | 128/200.23 |
| 5,031,610 | 7/1991 | Armstrong et al. | 128/200.23 |
| 5,060,643 | 10/1991 | Rich et al. | 128/200.23 |

Primary Examiner—Edgar S. Burr
Assistant Examiner—Aaron J. Lewis
Attorney, Agent, or Firm—Whitham & Marhoefer

[57] ABSTRACT

A single dose of a vaccine or other drug which is normally only given once is provided by an MDI by either formulating the drug and propellant composition to include only enough drug for one administration or by providing a locking mechanism to lock the MDI canister in a position where it cannot be actuated a second time.

5 Claims, 1 Drawing Sheet

SINGLE DOSE METERED DOSE INHALER FOR DELIVERY OF VACCINES AND OTHER DRUGS

BACKGROUND OF THE INVENTION

1. Field of the Invention

The present invention generally relates metered dose inhalers (MDIs) and, more particularly, to a single dose MDI for immunizing a patient with a vaccine by inhalation.

2. Description of the Prior Art

Currently, vaccines and other drugs are generally administered to patients by parenteral injection. The chief drawbacks of using injectable vaccines are that the route is invasive and inflicts pain as well as traumatic fright in children and some adults, and that the use of needles necessarily creates a disposal problem with related health hazards such as tuberculosis, AIDS, and other diseases.

Aerosol delivery of vaccines can eliminate both the invasiveness and disposal problems attributed to using injectable drugs. Much work has been done in establishing the efficacy of aerosol delivery of vaccines. For example, Dr. Albert Sabin has been working for several years with aerosol delivery of measles vaccines in third world countries. Even though there have been very effective vaccines for measles for many years, many children in impoverished countries, as well as urban centers in the United States, still die from the disease. Japanese and Russian researchers have also used aerosol delivery of measles vaccines. In addition to measles vaccines, there has been some recent experimentation with the delivery of rubella and attenuated influenza vaccines using aerosol delivery.

An MDI typically comprises a canister under pressure, fitted with a metering valve, which is filled with an aerosol formulation that includes a drug dissolved or dispersed in a propellant together with a surfactant. MDIs are in widespread use in the treatment of chronic disorders such as asthma and the like. The following drugs, as well as many others, are deliverable by MDIs: $\beta$-agonists such as albuterol (salbutamol), isoproterenol, ephedrine, epinephrine, salmeterol, terbutaline, and norepinephrine; corticosteroids such as triamcinolone acetonide, beclomethasone diproprionate, dexamethasone, and aldosterone; allergic mediators such as cromolyn sodium; antibiotics; and anticholinergics. MDIs are normally formulated with enough drug for the patient to take several doses of the drug over a given period of the time (e.g., a week, etc.).

Unlike chronic conditions such as asthma which require repetitive dosing of a drug, vaccinating a patient against a disease (e.g., measles, rubella, pertussis, AIDS, influenza, etc.) normally only requires one dose (sometimes two doses given a few months or years apart).

SUMMARY OF THE INVENTION

It is an object of this invention to provide an MDI which will provide a patient with a single dose of a vaccine or other drug which ordinarily only needs to be given one time.

According to the invention, a single dose is provided by an MDI by either formulating the drug and propellant composition to include only enough drug for one administration or by providing a locking mechanism to lock the MDI canister in a position where it cannot be actuated a second time.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENTS OF THE INVENTION

Figure 1:
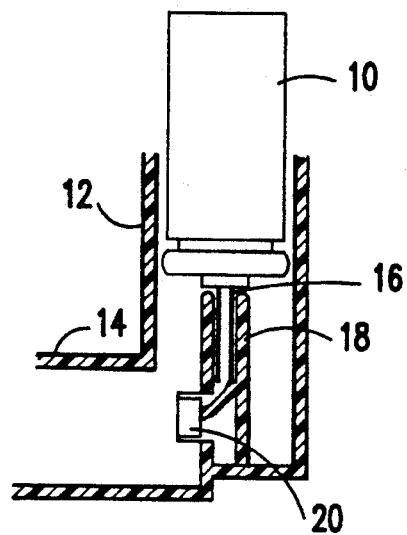
FIG. 1 is a schematic diagram of a metered dose inhaler.
Figures 2A, 2B:
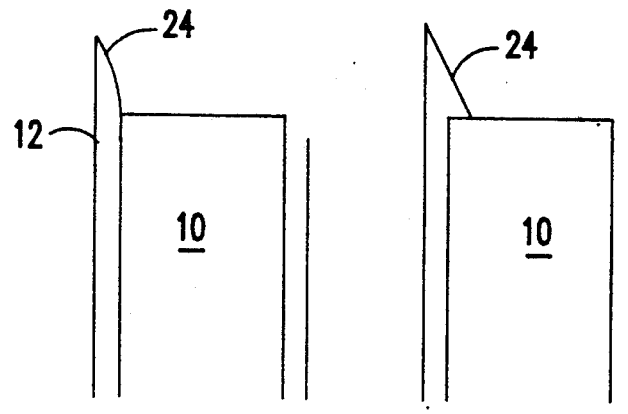
FIGS. 2a and 2b are sequential schematic diagrams of the rear portion of the canister in a metered dose inhaler showing a mechanical locking member being released to its locking position after one actuation of the canister.

With reference to the drawings, and FIG. 1 in particular, there is shown a typical MDI comprised of a canister 10 filled with a drug and propellant mixture, positioned with a body comprised of the canister guide tube 12 and the mouth piece 14. The valve stem 16 is positioned within valve seat 18. Pressing down on the canister 10 will force the valve stem 16 into the canister 10, and a metering arrangement within the canister 10 will allow a precise amount of drug and propellant out through the spray jet 20 for inspiration by the patient. An air inlet port 22 allows ambient air into the MDI device.

Figures 3A, 3B:
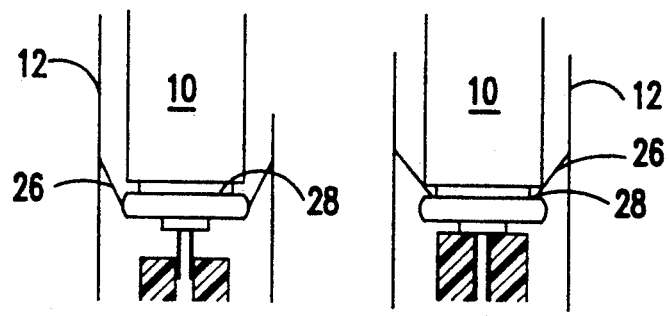
FIGS. 3a and 3b are sequential schematic diagrams of the side portion of the canister in a metered dose inhaler showing a mechanical locking mechanism allowing only one actuation of the canister.

This invention stems from the recognition that MDIs are likely to be superior vaccine delivery devices than the nebulizers used by prior researchers in the field of delivering vaccines by aerosol to the lungs. MDIs are self contained items which can provide for easy shipping and handling. In addition, MDIs can be administered by the user without the need for physician supervision.

Unlike most MDI products which provide repetitive drug doses several times a day or week to treat chronic conditions (e.g., albuterol or beclomethasone for asthma), vaccines are only used one time by a patient. Therefore, if a vaccine is to be administered by an MDI, it would be advantageous for the patient to only be permitted to provide himself or herself with one dose, thereby avoiding overdosing complications which might otherwise occur.

One embodiment of this invention contemplates formulating the drug/propellant composition in the canister 10 to include only one dose of drug. For example, a measles vaccination may normally include the equivalent of 1,000 tissue culture infectious doses ($TCID_{50}$) of the U.S. Reference Measles Virus. Therefore, only enough measles virus would provided in the canister 10 to provide the patient with the 1,000 $TCID_{50}$ of the measle virus, and no more measles virus will be present in the canister 10 after one actuation.

Another embodiment of this invention contemplates providing an MDI with a mechanical locking mechanism to prevent a second actuation of the canister 10. FIGS. 2*a* and 2*b* show a spring lock 24 connected to the canister guide tube 12. In the non-actuated position of FIG. 2*a*, the spring lock 24 is flexed against the side of the canister 24. FIG. 2*b* shows that after the canister 10 is pushed down one time, the spring lock 24 clears the rear end of the canister 10 and assumes its non-flexed configuration which locks the canister 10 in place. Suitable spring locks 24 could be made from plastic or metal materials. FIGS. 3a and 3b show a projection finger assembly 26 affixed to the inside wall of the canister guide tube 12. In the non-actuated position of FIG. 3a, the projection fingers 26 are flexed against the side of the canister 10. FIG. 3b shows that after actuation of the canister 10, the projection fingers interfit with the skirt region 28 of the canister 10 and prevent a second actuation. Obviously, other mechanisms which interact with the canister body could be devised.

While the invention has been described in terms of its preferred embodiments, those skilled in the art will recognize that the invention can be practiced with modification within the spirit and scope of the appended claims.

Having thus described our invention, what we claim and desire to secure by Letters Patent is as follows:

1. A metered dose inhaler, comprising:
   a canister filled with a drug composition or a vaccine and propellant;
   a metering valve connected to said canister to emit a single dose of said drug composition or said vaccine from said canister;
   a means for actuating said metering valve on said canister to release said single dose of said drug composition or vaccine from said canister; and
   a means for permanently preventing any quantity of said drug composition or said vaccine in excess of said single dose of said drug composition or said vaccine from being released from said canister after said means for actuating has been actuated.

2. A metered dose inhaler as recited in claim 1 wherein said means for permanently preventing includes a mechanical locking member which engages said canister after actuation and prevents any quantity of said drug composition of said vaccine in excess of said single dose of said drug composition or said vaccine from being released from said canister.

3. A metered dose inhaler as recited in claim 1 wherein said canister is filled with only enough drug composition or vaccine for a single dose and wherein said means for permanently preventing is inherent in said drug composition or said vaccine in said canister.

4. A metered dose inhaler as recited in claim 1 wherein said canister is filled with a vaccine.

5. A metered dose inhaler as recited in claim 4 wherein said vaccine is for immunization against measles.

* * * * *